United States Patent
Levy et al.

(10) Patent No.: US 11,918,420 B2
(45) Date of Patent: Mar. 5, 2024

(54) REFLECTION AUTOFOCUSING

(71) Applicant: INSIGHTEC, LTD., Tirat Carmel (IL)

(72) Inventors: Yoav Levy, Hinanit (IL); Oleg Prus, Hinanit (IL)

(73) Assignee: Insightec Ltd., Tirat Carmel (IL)

( * ) Notice: Subject to any disclaimer, the term of this patent is extended or adjusted under 35 U.S.C. 154(b) by 0 days.

(21) Appl. No.: 17/057,922

(22) PCT Filed: Jun. 5, 2019

(86) PCT No.: PCT/IB2019/000629
§ 371 (c)(1),
(2) Date: Nov. 23, 2020

(87) PCT Pub. No.: WO2019/234495
PCT Pub. Date: Dec. 12, 2019

(65) Prior Publication Data
US 2021/0196233 A1    Jul. 1, 2021

Related U.S. Application Data

(60) Provisional application No. 62/681,284, filed on Jun. 6, 2018.

(51) Int. Cl.
*A61B 8/08* (2006.01)
*A61B 5/055* (2006.01)
*A61N 7/00* (2006.01)

(52) U.S. Cl.
CPC ............ *A61B 8/5269* (2013.01); *A61B 8/481* (2013.01); *A61B 5/055* (2013.01);
(Continued)

(58) Field of Classification Search
CPC ........ A61B 8/4488; A61B 2018/00577; A61N 2007/0095; A61N 2007/0052; A61N 7/02; A61N 2007/0021; A61N 2007/0078
See application file for complete search history.

(56) References Cited

U.S. PATENT DOCUMENTS 5,921,932 A * 7/1999 Wright ................. G10K 11/346
600/447
6,666,833 B1 * 12/2003 Friedman ............. A61B 8/0808
600/407
(Continued)

FOREIGN PATENT DOCUMENTS

CN        101442938        5/2009
JP       2012-506736       3/2012
(Continued)

OTHER PUBLICATIONS

International Search Report and Written Opinion corresponding to International Application No. PCT/IB2019/000629, dated Nov. 26, 2019, 21 pages.
(Continued)

*Primary Examiner* — Joel Lamprecht
*Assistant Examiner* — Nyrobi Celestine
(74) *Attorney, Agent, or Firm* — Morgan, Lewis & Bockius LLP

(57) ABSTRACT

Various approaches for focusing an ultrasound transducer having multiple transducer elements include causing the transducer elements to transmit ultrasound waves to a target region and measure reflections of the ultrasound waves off the target region; for each of at least some of the transducer elements, adjusting a parameter value associated with said each transducer element based at least in part on parameter values associated with multiple measuring transducer elements weighted by signal quality metrics associated with the reflections measured by the measuring transducer elements so as to improve an ultrasound focus at the target region.

21 Claims, 9 Drawing Sheets

(52) U.S. Cl.
CPC ............... *A61N 2007/0039* (2013.01); *A61N 2007/0052* (2013.01); *A61N 2007/0095* (2013.01)

(56) References Cited

U.S. PATENT DOCUMENTS

| | | | | |
|---|---|---|---|---|
| 6,740,039 | B1* | 5/2004 | Rafter | A61B 8/463 |
| | | | | 600/439 |
| 8,357,094 | B2* | 1/2013 | Mo | G01S 7/5206 |
| | | | | 600/438 |
| 9,599,700 | B2* | 3/2017 | Tsao | A61B 8/54 |
| 9,918,701 | B2* | 3/2018 | Hedlund | A61B 8/54 |
| 2004/0122323 | A1* | 6/2004 | Vortman | A61N 7/02 |
| | | | | 600/459 |
| 2004/0210135 | A1 | 10/2004 | Kullervo et al. | |
| 2006/0052706 | A1* | 3/2006 | Hynynen | A61N 7/022 |
| | | | | 600/459 |
| 2009/0069692 | A1* | 3/2009 | Cooley | G01S 7/52095 |
| | | | | 600/459 |
| 2010/0106019 | A1 | 4/2010 | Barry et al. | |
| 2011/0288450 | A1* | 11/2011 | Cerwin | A61N 7/00 |
| | | | | 601/2 |
| 2013/0150756 | A1 | 6/2013 | Shuki et al. | |
| 2013/0253325 | A1* | 9/2013 | Call | A61B 8/5253 |
| | | | | 600/447 |
| 2014/0243667 | A1* | 8/2014 | Wilkening | A61N 7/00 |
| | | | | 600/438 |
| 2015/0165242 | A1* | 6/2015 | Zeng | A61N 7/02 |
| | | | | 601/3 |
| 2016/0054435 | A1* | 2/2016 | Kim | G01S 7/52047 |
| | | | | 367/138 |
| 2016/0184026 | A1* | 6/2016 | Tlusty | A61B 6/037 |
| | | | | 600/407 |
| 2017/0209121 | A1* | 7/2017 | Davis, Sr. | A61B 8/4494 |
| 2018/0175942 | A1* | 6/2018 | Bandy | H04W 72/0453 |
| 2018/0188104 | A1* | 7/2018 | Arai | G10K 11/346 |
| 2018/0242951 | A1* | 8/2018 | Hiroshima | G01S 7/52026 |
| 2019/0308038 | A1 | 10/2019 | Prus et al. | |
| 2019/0311478 | A1* | 10/2019 | Avendi | G06K 9/6289 |
| 2020/0268356 | A1* | 8/2020 | Li | A61B 8/54 |

FOREIGN PATENT DOCUMENTS

| | | | |
|---|---|---|---|
| JP | 2015-512301 | 4/2015 | |
| WO | WO-2013108152 A1 * | 7/2013 | ............... A61N 7/02 |
| WO | WO2018/020315 A1 | 2/2018 | |

OTHER PUBLICATIONS

Invitation to Pay Additional Fees corresponding to International Application No. PCT/IB2019/000629, dated Nov. 18, 2019, 14 pgs.
International Preliminary Report on Patentability corresponding to International Application No. PCT/IB2019/000629, dated Dec. 8, 2020, 15 pgs.
Insightec, Ltd., First Office Action, CN201980052186.6, dated Jul. 27, 2022, 10 pgs.
Insightec, Ltd., Notice of Reasons for Rejection, JP2020-567742, dated Jul. 20, 2022, 13 pgs.
Notice of Reasons for Rejection with English translation for corresponding Japanese Patent Application No. 2020-567742 dated Feb. 14, 2023, 9 pages.
Notice of Second Office Action with English translation, dated Feb. 2, 2023, for corresponding Chinese Patent Application No. 201980052186.6, 9 pages.

* cited by examiner

REFLECTION AUTOFOCUSING

CROSS-REFERENCE TO RELATED APPLICATION

This application is a U.S. National Phase Application of PCT/IB2019/000629, filed Jun. 5, 2019, which claims priority to and the benefits of U.S. Provisional Patent Application No. 62/681,284, which was filed on Jun. 6, 2018. The entire disclosures of these priority documents are hereby incorporated by reference in their entireties.

FIELD OF THE INVENTION

The present invention relates, generally, to systems and methods for ultrasound autofocusing and, more particularly, to improved autofocusing using ultrasound reflections.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (Mill) may be used to visualize the patient and target, and thereby to guide the ultrasound beam.

During a focused ultrasound procedure, a series of sonications is applied to cause coagulation necrosis of the target tissue (such as a tumor) without damaging surrounding tissue. To achieve this, ultrasonic energy emitted from the transducer must be accurately and reliably shaped and focused onto the desired target location. Transducer elements that are not properly configured can lead to improper focal qualities, thereby causing ineffective treatment and/or undesired damage to the non-target tissue. In addition, improperly shaped ultrasound beams may generate unexpected, secondary hot spots at locations other than the intended focal zone; such hot spots may lead to undesired heating, pain for the patient, and/or possibly necrosis of non-targeted tissue.

One source of transducer output errors results from geometric imperfections in the transducer elements (i.e., deviations from their expected locations). For example, assuming a transducer is designed to have a spherical shape, the software that drives each transducer element is configured to activate individual transducer elements based on their positioning according to a spherical model or design. To the extent that the actual location of one or more transducer elements is shifted from the expected location during manufacture, use and/or repair, or if the location shifts as a result of, for example, deformation by heat, the result can be permanent focusing errors due to software programmed according to an ideal spherical model.

Another source of transducer output errors is inhomogeneity of the intervening tissue through which the ultrasound waves travel prior to reaching the focal zone. The ultrasound waves may interact with the intervening tissue through multiple processes, including propagation, scattering, absorption, reflection, and refraction. For example, inhomogeneity of the tissue may cause refraction of acoustic energy at the boundaries of regions that have different speeds of sound. Refraction may decrease constructive interference, and hence, the intensity of the acoustic energy at the focal zone. Thus, an inhomogeneous tissue may generate beam aberrations and refractions that distort the focus and reduce its intensity, thereby affecting treatment efficiency.

One approach for calibrating the transducer geometric errors and/or beam aberrations resulting from the intervening tissue involves placing or generating an acoustic reflector at the focal point. Reflected signals from the reflector may be detected by the transducer elements, and the deviations between the phases of the reflected signals measured by the transducer elements and the phases of the transmitting signals can be determined. Based on the determined deviations, the drive signal associated with the transducer elements can be adjusted to improve focusing properties.

While this approach may effectively compensate for the phase deviations and improve focusing properties at the target region, it may be applicable to only some transducer elements in the transducer array. For example, in treatment of a brain tumor, some transducer elements may receive poor-quality (e.g., low signal-to-noise ratio (SNR)) signals due to the nature of the skull and its multiple-layered internal structure; this causes the echo-signal measurements to be unreliable. Accordingly, the ability to compensate for phase deviations for the transducer elements that receive low-quality echo signals would be critical to further improve focusing properties at the target region.

In addition, because the focusing approach described above may require several iterations of the echo-signal measurements for phase corrections, it may be time-consuming when the treatment involves multiple discontiguous regions and each of them requires separate echo-signal measurements for phase corrections. Thus, a need exists for approaches that create a high-quality ultrasound focus at each of the multiple target regions and obviate the need to measure echo signals and perform the focusing procedure for each individual target.

SUMMARY

The present invention provides systems and methods for driving all transducer elements in a transducer array with ultrasound parameters that account for transducer geometric errors and/or beam aberrations resulting from intervening tissues so as to create a high-quality focus at one or more target regions. As used herein, the term "high-quality focus" refers to a focus having a sufficiently small focal zone corresponding to a sufficiently high acoustic intensity for the purpose of ultrasound treatment; this is different from the conventional definition where the focal quality is related to the degree of conformity of the focal area to a desired shape (e.g., a line focus). In various embodiments, an acoustic reflector (e.g., a volume of microbubbles) is introduced in a focal zone that is substantially close to the target region; ultrasound signals reflected from the acoustic reflector are first analyzed to determine the quality (e.g., the SNR) thereof. If the received signals have sufficient quality (e.g., the SNRs are equal to or above a predetermined threshold), the signals may be further analyzed to acquire ultrasound parameter values (e.g., phases, amplitudes and/or frequencies) associated therewith; subsequently, the transducer elements that receive the sufficient-quality signals may be driven based on the acquired ultrasound parameter values. Alternatively or additionally, the quality of the reflection signals may be determined based on the repetitiveness of ultrasound parameter values obtained using the reflection signals received in several measurements. For example, if the ultrasound parameter values determined in repetitive measurements are substantially similar (e.g., having a difference therebetween within 10%), the reflection signals are classified as having sufficient quality.

If, however, the received signals have low quality (e.g., the SNRs are below the predetermined threshold) and/or low repetitiveness of the quality (e.g., the differences among the determined ultrasound parameter values in repetitive measurements equal or exceed 10% of one of the determined ultrasound parameter values), various approaches may be implemented to correct or update the ultrasound parameter values associated with the transducer elements that receive these signals. For example, a physical model may be utilized to predict the ultrasound parameter values. The physical model may employ an acoustic ray model to simulate the beam paths of ultrasound waves from the transducer elements to the target region. In addition, the acoustic ray model may take into account beam aberrations (e.g., refraction) resulting from the intervening tissues and adjust the beam paths to account for the aberrations. Further, the physical model may include a focusing algorithm to determine the ultrasound parameter values associated with the transducer elements that receive the low-quality signals based on the predicted beam paths.

Additionally or alternatively, the reflection signals that have sufficient quality may be utilized to optimize or improve the physical model so as to improve prediction of the ultrasound parameter values associated with the transducer elements receiving the low-quality reflection signals. In one embodiment, the ultrasound parameter values associated with the reflection signals having sufficient quality may be provided to the physical model to inversely compute values of the model parameters. Because the measured reflection signals include the effects on beams from the intervening tissues, the physical model having parameter values based thereon is improved/optimized to more accurately predict the ultrasound parameter values associated with the transducer elements that receive the low-quality signals.

In some embodiments, a machine-learning process (e.g., a neural network) is implemented to predict the ultrasound parameter values associated with the transducer elements receiving low-quality signals. For example, reflection signals having sufficient quality and various characteristics of the intervening tissues along the paths of the reflection signals may form a training set. Using the training set, a relationship between the tissue characteristics and measured ultrasound parameter values can be determined by training the neural network. The trained neural network may then predict the ultrasound parameter values associated with the transducer elements receiving the low-quality signals based on the characteristics of the intervening tissues along their paths.

In another embodiment, the ultrasound parameter values associated with the transducer elements receiving low-quality reflection signals are determined based on the measured reflection signals having sufficient quality and the difference between (i) the distance from the target region to the transducer elements that receive reflection signals having sufficient quality and (ii) the distance from the target region to the transducer elements that receive reflection signals having low quality.

Accordingly, the present invention provides various approaches that advantageously allow transmitted waves from additional transducer elements in a transducer array to be compensated for the transducer geometric imperfections and/or beam aberrations resulting from the intervening tissue; this may significantly improve the focusing properties at the target region.

In various embodiments, the ultrasound treatment involves multiple target regions; the above-described approaches may be implemented to determine the ultrasound parameter values of the transducer elements for generating a high-quality focus at one target region based on the received reflection signals from another target region. For example, the received reflection signals from the first target region may be used to improve the physical model and/or train the neural network, which can then predict the ultrasound parameter values for generating the focus at the second target region. In some embodiments, the ultrasound parameter values associated with the second target region are determined based on the measured reflections signals from the first target region and a difference between the distance from each transducer element to the first target region and the distance from each transducer element to the second target region.

Accordingly, the present invention also provides various approaches that allow high-quality ultrasound foci to be created at multiple target regions without the need to measure reflection signals from individual target regions and performing the focusing procedure. This may significantly reduce the treatment time.

Accordingly, in one aspect, the invention pertains to a system for focusing an ultrasound transducer. In various embodiments, the system includes an ultrasound transducer having multiple transducer elements; and a controller configured to (a) cause the transducer elements to transmit ultrasound waves to a target region and measure reflections of the ultrasound waves off the target region; and (b) for each of at least some of the transducer elements, adjust a parameter value (e.g., a frequency, an amplitude and/or a phase) associated with said each transducer element based at least in part on parameter values associated with multiple measuring transducer elements weighted at least in part by signal quality metrics associated with the reflections measured by the measuring transducer elements so as to improve an ultrasound focus at the target region. In one implementation, the measuring transducer elements are different from said each transducer element. The signal quality metric may be a signal-to-noise ratio of the measured reflections. Additionally or alternatively, the quality metric may be repetitiveness of the parameter value associated with one of the measuring transducer elements determined based on the measured reflections in multiple measurements.

The controller may be further configured to define a weighting vector having values of zero corresponding to at least some of the measuring transducer elements upon determining that the signal quality metric associated with the reflections measured by the at least some of the measuring transducer element is below a predetermined threshold. In addition, the controller may be further configured to define a weighting vector having values greater than zero and less than or equal to one corresponding to at least some of the measuring transducer elements upon determining that the signal quality metric associated with the reflections measured by the at least some of the measuring transducer element equals to or exceeds a predetermined threshold. In one embodiment, the controller is further configured to weight the parameter values associated with the measuring transducer at least in part by distances of the measuring transducer elements from said each transducer element. For example, the weighting values corresponding to the measuring transducer elements may negatively correlate to the distances of the measuring transducer elements from said each transducer element.

In various embodiments, the controller is further configured to cause generation of one or more acoustic reflectors (e.g., microbubbles) in the target region using the ultrasound transducer. Additionally or alternatively, the system may further include an administration device for introducing the acoustic reflector(s) into the target region. In one embodiment, the administration device introduces a seed microbubble into the target region; the controller is further configured to cause generation of the acoustic reflector(s) using the seed microbubble and the ultrasound transducer. The acoustic reflector(s) may reflect the ultrasound waves transmitted thereto.

In some embodiments, the controller is further configured to adjust one or more parameter values (e.g., a frequency, an amplitude and/or a phase) associated with one or more of the measuring transducer elements based at least in part on the reflections measured thereby. In addition, the controller may be further configured to adjust the parameter value(s) associated with said each transducer element based at least in part on a physical model. The physical model may include multiple model parameters; the controller is further configured to determine values associated with the model parameters based at least in part on the reflections measured by one or more of the measuring transducer elements. Additionally or alternatively, the controller may be further configured to adjust the parameter value associated with said each transducer element based at least in part on a predictor that has been computationally trained to predict the parameter value based on a characteristic (e.g., the type, size, location, property, structure, thickness, density, structure, etc.) of an intervening tissue located between said each transducer element and the target region. For example, the controller may be further configured to computationally train the predictor using the reflections measured by one or more of the measuring transducer elements and the characteristic of the intervening tissue located between the measuring transducer element(s) and the target region. In addition, the system may further include an imaging modality (e.g., MRI apparatus) for acquiring the characteristic of the intervening tissue.

In various embodiments, the controller is further configured to compute the first phase associated with one of the measuring transducer elements and the second phase associated with said each transducer element; and adjust the parameter value associated with said each transducer element based at least in part on the computed first and second phases. In addition, the controller may be further configured to compute a difference between the first and second phases based at least in part on the difference between the first distance from the measuring transducer element to the target and the second distance from said each transducer element to the target. In one embodiment, the controller is further configured to compute the first phase based at least in part on a characteristic (e.g., the type, size, location, property, structure, thickness, density, etc.) of an intervening tissue located between the measuring transducer element and the target region along a beam path associated with the reflections measured by the measuring transducer element.

In another aspect, the invention relates to a method of focusing an ultrasound transducer having multiple transducer elements. In various embodiments, the method includes causing the transducer elements to transmit ultrasound waves to a target region and measure reflections of the ultrasound waves off the target region; and for each of at least some of the transducer elements, adjusting a parameter value (e.g., a frequency, an amplitude and/or a phase) associated with said each transducer element based at least in part on parameter values associated with multiple measuring transducer elements weighted at least in part by signal quality metrics associated with the reflections measured by the measuring transducer elements so as to improve an ultrasound focus at the target region. In one implementation, the measuring transducer elements are different from said each transducer element. The signal quality metric may be a signal-to-noise ratio of the measured reflections. Additionally or alternatively, the quality metric may be repetitiveness of the parameter value associated with one of the measuring transducer elements determined based on the measured reflections in multiple measurements.

The method may further include defining a weighting vector having values of zero corresponding to at least some of the measuring transducer elements upon determining that the signal quality metric associated with the reflections measured by the at least some of the measuring transducer element is below a predetermined threshold. In addition, the method may further include defining a weighting vector having values greater than zero and less than or equal to one corresponding to at least some of the measuring transducer elements upon determining that the signal quality metric associated with the reflections measured by the at least some of the measuring transducer element equals to or exceeds a predetermined threshold. In one embodiment, the method further includes weighting the parameter values associated with the measuring transducer elements at least in part by distances of the measuring transducer elements from said each transducer element. For example, the weighting values corresponding to the measuring transducer elements may negatively correlate to the distances of the measuring transducer elements from said each transducer element.

In various embodiments, the method further includes causing generation of one or more acoustic reflectors (e.g., microbubbles) in the target region using the ultrasound transducer. Additionally or alternatively, the method may further include introducing the acoustic reflector(s) into the target region. In one embodiment, the method further includes introducing a seed microbubble into the target region, and causing generation of the acoustic reflector(s) using the seed microbubble and the ultrasound transducer. The acoustic reflector(s) may reflect the ultrasound waves transmitted thereto.

In some embodiments, the method further includes adjusting one or more parameter values (e.g., a frequency, an amplitude and/or a phase) associated with one or more of the measuring transducer elements based at least in part on the reflections measured thereby. In addition, the method may further include adjusting the parameter value associated with said each transducer element based at least in part on a physical model. The physical model may include multiple model parameters; the method further includes determining values associated with the model parameters based at least in part on the reflections measured by one or more of the measuring transducer elements. Additionally or alternatively, the method may further includes adjusting the parameter value associated with said each transducer element based at least in part on a predictor that has been computationally trained to predict the parameter value based on a characteristic (e.g., the type, size, location, property, structure, thickness, density, etc.) of an intervening tissue located between said each transducer element and the target region. For example, the method may further include computationally training the predictor using the reflections measured by one or more of the measuring transducer elements and the characteristic of the intervening tissue located between the measuring transducer element(s) and the target region. In addition, the method may include acquiring the characteristic of the intervening tissue using an imaging modality (e.g., MRI apparatus).

In various embodiments, the method further includes computing the first phase associated with one of the measuring transducer elements and the second phase associated with said each transducer element; and adjusting the parameter value associated with said each transducer element based at least in part on the computed first and second phases. In addition, the method may further include computing a difference between the first and second phases based at least in part on the difference between the first distance from the measuring transducer element to the target and the second distance from said each transducer element to the target. In one embodiment, the method further includes computing the first phase based at least in part on a characteristic (e.g., the type, size, location, property, structure, thickness, density, etc.) of an intervening tissue located between the measuring transducer element and the target region along a beam path associated with the reflections measured by the measuring transducer element.

Another aspect of the invention relates to a system for focusing an ultrasound transducer. In various embodiments, the system includes an ultrasound transducer having multiple transducer elements; and a controller configured to (a) cause the transducer elements to transmit ultrasound waves to a target region and measure reflections of the ultrasound waves off the target region; (b) define a remediation set of the transducer elements based on measured reflections having a quality metric below a predetermined threshold; (c) for the first one or more of the transducer elements in the remediation set, determine the second one or more of the transducer elements that are not in the remediation set; and (d) based at least in part on the measured reflections associated with the second one(s) of the transducer elements, adjust a parameter value (e.g., a frequency, an amplitude and/or a phase) associated with the first one(s) of the transducer elements in the remediation set so as to improve an ultrasound focus at the target region. The signal quality metric may be a signal-to-noise ratio of the measured reflections. Additionally or alternatively, the quality metric may be repetitiveness of the parameter value associated with the second one(s) of the transducer elements determined based on the measured reflections in multiple measurements.

The second one(s) of the transducer elements may be located within a predetermined distance from the first one(s) of the transducer elements. In addition, the second one(s) of the transducer elements may be associated with the measured reflections having the quality metric equal to or exceeding the predetermined threshold. In various embodiments, the controller is further configured to cause generation of one or more acoustic reflectors (e.g., microbubbles) in the target region using the ultrasound transducer, the acoustic reflector reflecting the ultrasound waves transmitted thereto. Additionally or alternatively, the system may further include an administration device for introducing the acoustic reflector(s) into the target region. In one embodiment, the administration device introduces a seed microbubble into the target region; the controller is further configured to cause generation of the acoustic reflector(s) using the seed microbubble and the ultrasound transducer. The acoustic reflector(s) may reflect the ultrasound waves transmitted thereto.

In some embodiments, the controller is further configured to adjust one or more parameter values (e.g., a frequency, an amplitude and/or a phase) associated with the second one(s) of the transducer elements based at least in part on the reflections measured thereby. In addition, the controller may be further configured to adjust the parameter value associated with the first one(s) of the transducer elements in the remediation set based at least in part on a physical model. The physical model may include multiple model parameters; the controller is further configured to determine values associated with the model parameters based at least in part on the reflections measured by the second one(s) of the transducer elements. Additionally or alternatively, the controller may be further configured to adjust the parameter value associated with the first one(s) of the transducer elements in the remediation set based at least in part on a predictor that has been computationally trained to predict the parameter value based on a characteristic (e.g., the type, size, location, property, structure, thickness, density, etc.) of an intervening tissue located between the first one(s) of the transducer elements and the target region. For example, the controller may be further configured to computationally train the predictor using the reflections measured by the second one(s) of the transducer elements and the characteristic of the intervening tissue located between the second one(s) of the transducer elements and the target region. In addition, the system may further include an imaging modality for acquiring the characteristic of the intervening tissue.

In various embodiments, the controller is further configured to compute the first phase associated with the second one(s) of the transducer elements and the second phase associated with the first one(s) of the transducer elements in the remediation set; and adjust the parameter value associated with the first one(s) of the transducer element in the remediation set based at least in part on the computed first and second phases. In addition, the controller may be further configured to compute a difference between the first and second phases based at least in part on the difference between the first distance from the first one(s) of the transducer elements in the remediation set to the target and the second distance from the second one(s) of the transducer elements to the target. In one embodiment, the controller is further configured to compute the second phase based at least in part on a characteristic of an intervening tissue located between the ultrasound transducer and the target region along a beam path associated with the reflections measured by the second one(s) of the transducer elements.

In yet another aspect, the invention pertains to a method of focusing an ultrasound transducer having multiple transducer elements. In various embodiments, the method includes (a) causing the transducer elements to transmit ultrasound waves to a target region and measure reflections of the ultrasound waves off the target region; (b) defining a remediation set of the transducer elements based on measured reflections having a quality metric below a predetermined threshold; (c) for the first one or more of the transducer elements in the remediation set, determining the second one or more of the transducer elements that are not in the remediation set; and (d) based at least in part on the measured reflections associated with the second one(s) of the transducer elements, adjusting a parameter value (e.g., a frequency, an amplitude and/or a phase) associated with the first one(s) of the transducer elements in the remediation set so as to improve an ultrasound focus at the target region. The signal quality metric may be a signal-to-noise ratio of the measured reflections. Additionally or alternatively, the quality metric may be repetitiveness of the parameter value associated with the second one(s) of the transducer elements determined based on the measured reflections in multiple measurements.

The second one(s) of the transducer elements may be located within a predetermined distance from the first one(s) of the transducer elements. In addition, the second one(s) of the transducer elements may be associated with the measured reflections having the quality metric equal to or exceeding the predetermined threshold. In various embodiments, the method further includes causing generation of one or more acoustic reflectors (e.g., microbubbles) in the target region using the ultrasound transducer. Additionally or alternatively, the method may further include introducing the acoustic reflector(s) into the target region. In one embodiment, the method further includes introducing a seed microbubble into the target region, and causing generation of the acoustic reflector(s) using the seed microbubble and the ultrasound transducer. The acoustic reflector(s) may reflect the ultrasound waves transmitted thereto.

In some embodiments, the method further includes adjusting one or more parameter values (e.g., a frequency, an amplitude and/or a phase) associated with the second one(s) of the transducer elements based at least in part on the reflections measured thereby. In addition, the method may further include adjusting the parameter value associated with the first one(s) of the transducer elements in the remediation set based at least in part on a physical model. The physical model may include multiple model parameters; the method further includes determining values associated with the model parameters based at least in part on the reflections measured by the second one(s) of the transducer elements. Additionally or alternatively, the method may further includes adjusting the parameter value associated with the first one(s) of the transducer elements in the remediation set based at least in part on a predictor that has been computationally trained to predict the parameter value based on a characteristic (e.g., the type, size, location, property, structure, thickness, density, etc.) of an intervening tissue located between the first one(s) of the transducer elements and the target region. For example, the method may further include computationally training the predictor using the reflections measured by the second one(s) of the transducer elements and the characteristic of the intervening tissue located between the second one(s) of the transducer element(s) and the target region. In addition, the method may include acquiring the characteristic of the intervening tissue using an imaging modality (e.g., MRI apparatus).

In various embodiments, the method further includes computing the first phase associated with the second one(s) of the transducer elements and the second phase associated with the first one(s) of the transducer elements in the remediation set, respectively; and adjusting the parameter value associated with the first one(s) of the transducer element in the remediation set based at least in part on the computed first and second phases. In addition, the method may further include computing a difference between the first and second phases based at least in part on the difference between the first distance from the first one(s) of the transducer elements in the remediation set to the target and the second distance from the second one(s) of the transducer elements to the target. In one embodiment, the method further includes computing the second phase based at least in part on a characteristic (e.g., the type, size, location, property, structure, thickness, density, etc.) of an intervening tissue located between the ultrasound transducer and the target region along a beam path associated with the reflections measured by the second one(s) of the transducer elements.

Still another aspect of the invention relates to a system for focusing an ultrasound transducer. In various embodiments, the system includes an ultrasound transducer having multiple transducer elements; and a controller configured to (a) cause the transducer elements to transmit ultrasound waves to a target region and measure reflections of the ultrasound waves off the target region; (b) determine the first parameter value (e.g., a frequency, an amplitude and/or a phase) associated with the first one or more of the transducer elements based at least in part on the reflections measured thereby; (c) predict the second parameter value (e.g., a frequency, an amplitude and/or a phase) associated with the second one or more of the transducer elements, different from the first one(s) of the transducer elements, based at least in part on a characteristic (e.g., the type, size, location, property, structure, thickness, density, etc.) of an intervening tissue located between the second one(s) of the transducer elements and the target region; and (d) drive the first and second ones of the transducer elements so as to create an ultrasound focus at the target region. In one implementation, the first one(s) of the transducer elements receives the reflections having a quality metric equal to or exceeding a predetermined threshold, and the second one(s) of the transducer elements receives the reflections having a quality metric below a predetermined threshold.

In another aspect, the invention relates to a method for focusing an ultrasound transducer having multiple transducer elements. In various embodiments, the method includes (a) causing the transducer elements to transmit ultrasound waves to a target region and measure reflections of the ultrasound waves off the target region; (b) determining the first parameter value (e.g., a frequency, an amplitude and/or a phase) associated with the first one or more of the transducer elements based at least in part on the reflections measured thereby; (c) predicting the second parameter value (e.g., a frequency, an amplitude and/or a phase) associated with the second one or more of the transducer elements, different from the first one(s) of the transducer elements, based at least in part on a characteristic (e.g., the type, size, location, property, structure, thickness, density, etc.) of an intervening tissue located between the second one(s) of the transducer elements and the target region; and (d) driving the first and second ones of the transducer elements so as to create an ultrasound focus at the target region. In one implementation, the first one(s) of the transducer elements receives the reflections having a quality metric equal to or exceeding a predetermined threshold, and the second one(s) of the transducer elements receives the reflections having a quality metric below a predetermined threshold.

In still another aspect, the invention relates to a system for focusing an ultrasound transducer. In various embodiments, the system includes an ultrasound transducer having multiple transducer elements; and a controller configured to (a) cause the transducer elements to transmit ultrasound waves to the first one or more target regions and measure reflections of the ultrasound waves off the first target region(s); and (b) based at least in part on the measured reflections, determine a parameter value (e.g., a frequency, an amplitude and/or a phase) associated with one or more of the transducer elements so as to generate an ultrasound focus at the second target region, different from the first target region(s).

In various embodiments, the controller is further configured to cause generation of one or more acoustic reflectors (e.g., microbubbles) in the first target region(s) using the ultrasound transducer. Additionally or alternatively, the system further includes an administration device for introducing the acoustic reflector(s) into the first target region(s). In one embodiment, the administration device introduces a seed microbubble into the first target region(s); the controller is further configured to cause generation of the acoustic reflector(s) using the seed microbubble and the ultrasound transducer. The acoustic reflector(s) may reflect the ultrasound waves transmitted thereto.

In some embodiments, the controller is further configured to determine the parameter value based at least in part on a predictor that has been computationally trained to predict the parameter value based on a characteristic (e.g., the type, size, location, property, structure, thickness, density, etc.) of an intervening tissue located between the ultrasound transducer and the second target region. For example, the controller may be further configured to computationally train the predictor using the measured reflections off the first target region(s) and the characteristic of the intervening tissue located between the ultrasound transducer and the first target region(s). In addition, the system may further include an imaging modality (e.g., MM apparatus) for acquiring the characteristic of the intervening tissue. Additionally or alternatively, the controller may be further configured to determine a parameter value (e.g., a frequency, an amplitude and/or a phase) associated with one or more of the transducer elements based at least in part on a physical model. The physical model may include multiple model parameters; the controller is further configured to determine values associated with the model parameters based at least in part on the measured reflections of the ultrasound waves off the first target region(s).

In various embodiments, the controller is further configured to compute the first phase and the second phase associated with the first target region(s) and the second target region, respectively; and determine the parameter value based at least in part on the computed first and second phases. In addition, the controller may be further configured to compute a difference between the first and second phases based at least in part on the difference between the first distance from the ultrasound transducer to the first target region(s) and the second distance from the ultrasound transducer to the second target region. In one embodiment, the controller is further configured to compute the first phase based at least in part on a characteristic (e.g., the type, size, location, property, structure, thickness, density, etc.) of an intervening tissue located between the ultrasound transducer and the first target region(s) along a beam path associated with the reflections off the first target region(s) to the ultrasound transducer.

In another aspect, the invention pertains to a method of focusing an ultrasound transducer having multiple transducer elements. In various embodiments, the method includes (a) causing the transducer elements to transmit ultrasound waves to the first one or more target regions and measure reflections of the ultrasound waves off the first target region(s); and (b) based at least in part on the measured reflections, determining a parameter value (e.g., a frequency, an amplitude and/or a phase) associated with one or more of the transducer elements so as to generate an ultrasound focus at the second target region different from the first target region(s).

In various embodiments, the method further includes causing generation of one or more acoustic reflectors (e.g., microbubbles) in the first target region(s) using the ultrasound transducer. Additionally or alternatively, the method may further include introducing the acoustic reflector(s) into the target region(s). In one embodiment, the method further includes introducing a seed microbubble into the first target region(s), and causing generation of the acoustic reflector(s) using the seed microbubble and the ultrasound transducer. The acoustic reflector(s) may reflect the ultrasound waves transmitted thereto.

In some embodiments, the method further includes determining the parameter value based at least in part on a predictor that has been computationally trained to predict the parameter value based on a characteristic (e.g., the type, size, location, property, structure, thickness, density, etc.) of an intervening tissue located between the ultrasound transducer and the second target region. For example, the method may further include computationally training the predictor using the measured reflections off the first target region(s) and the characteristic of the intervening tissue located between the ultrasound transducer and the first target region (s). In addition, the method may further include acquiring the characteristic of the intervening tissue using an imaging modality (e.g., MRI apparatus). Additionally or alternatively, the method may further include determining a parameter value (e.g., a frequency, an amplitude and/or a phase) associated with one or more of the transducer elements based at least in part on a physical model. The physical model may include multiple model parameters; the method further includes determining values associated with the model parameters based at least in part on the measured reflections of the ultrasound waves off the first target region(s).

In various embodiments, the method further includes computing the first phase and the second phase associated with the first target region(s) and the second target region, respectively; and determining the parameter value based at least in part on the computed first and second phases. In addition, the method may further include computing a difference between the first and second phases based at least in part on the difference between the first distance from the ultrasound transducer to the first target region(s) and the second distance from the ultrasound transducer to the second target region. In one embodiment, the method further includes computing the first phase based at least in part on a characteristic (e.g., the type, size, location, property, structure, thickness, density, etc.) of an intervening tissue located between the ultrasound transducer and the first target region(s) along a beam path associated with the reflections off the first target region(s) to the ultrasound transducer.

As used herein, "low-quality" or "poor-quality" signals refer to signals having poor quality (e.g., the SNRs are below a first predetermined threshold) and/or low repetitiveness of the quality (e.g., the differences among the determined ultrasound parameter values in repetitive measurements equal or exceed a second predetermined threshold, such as 10%, of one of the determined ultrasound parameter values); whereas sufficient-quality signals or high-quality signals refer to signals having sufficient quality (e.g., the SNRs are equal to or above a first predetermined threshold) and/or high repetitiveness of the quality (e.g., the differences among the determined ultrasound parameter values in repetitive measurements are below a second predetermined threshold, such as 10%, of one of the determined ultrasound parameter values). In addition, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
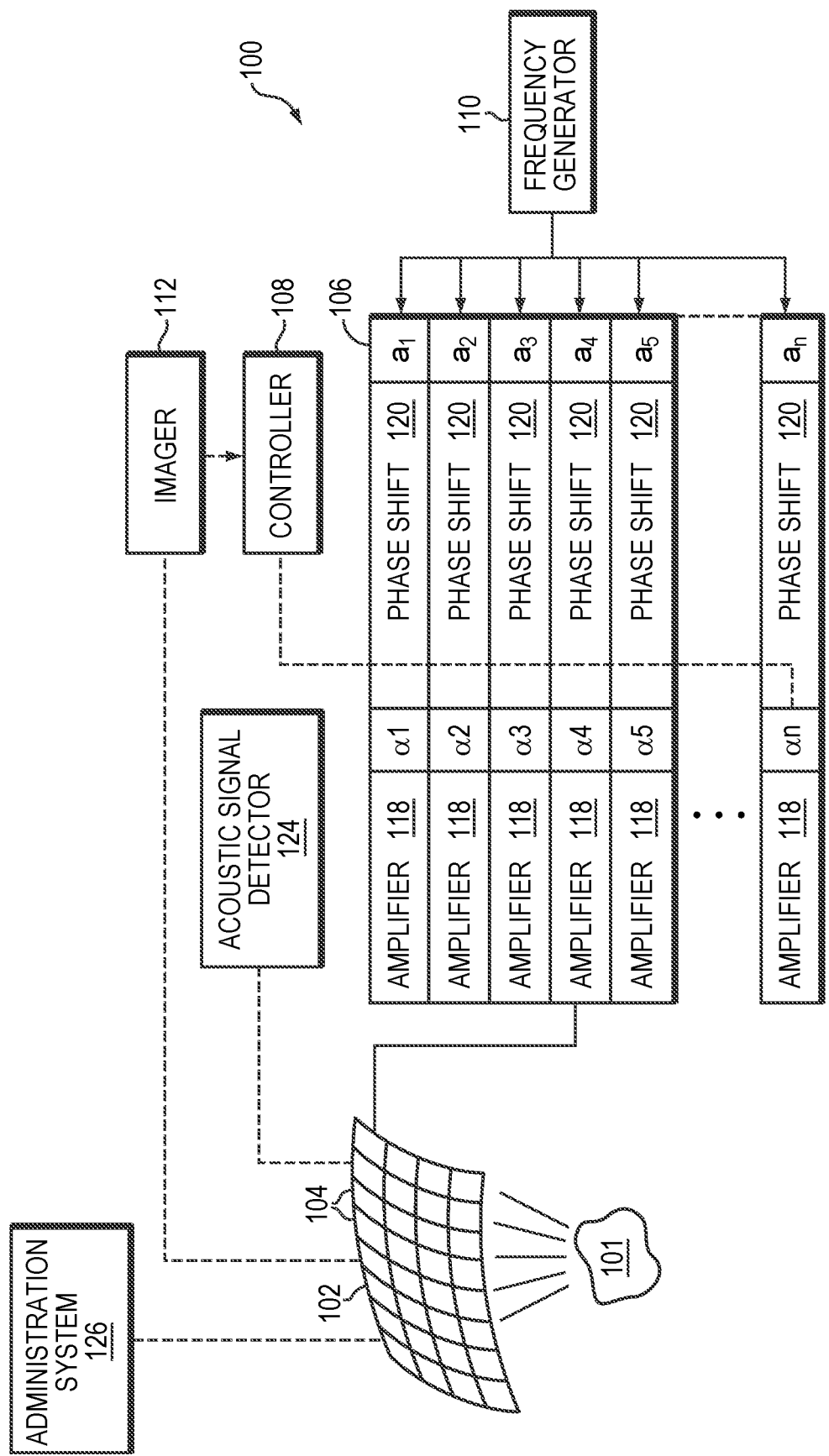
FIG. 1A schematically depicts an exemplary ultrasound system in accordance with various embodiments of the current invention.

FIG. 1A illustrates an exemplary ultrasound system 100 for generating and delivering a focused acoustic energy beam to a target region 101 within a patient's body. The illustrated system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) or other contoured shape suitable for placement on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $\alpha_1$-$\alpha_n$ imposed by the beamformer 106 serve to transmit and focus ultrasonic energy through the intervening tissue located between the transducer elements 104 and the target region onto the target region 101, and account for wave distortions induced in the intervening tissue. The amplification factors and phase shifts are computed using the controller 108, which may provide the computational functions through software, hardware, firmware, hardwiring, or any combination thereof. In various embodiments, the controller 108 utilizes a general-purpose or special-purpose digital data processor programmed with software in a conventional manner, and without undue experimentation, to determine the frequency, phase shifts and/or amplification factors necessary to obtain a desired focus or any other desired spatial field patterns at the target region 101. In certain embodiments, the computation is based on detailed information about the characteristics (e.g., the type, size, location, property, structure, thickness, density, etc.) of the intervening tissue located between the transducer element 104 and the target and their effects on propagation of acoustic energy. Such information may be obtained from an imager 112. The imager 112 may be, for example, a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 112 may provide a set of two-dimensional (2D) images suitable for reconstructing a three-dimensional image of the target region 101 and/or other regions (e.g., the region surrounding the target 101 or another target region). Image-manipulation functionality may be implemented in the imager 112, in the controller 108, or in a separate device. In addition, the ultrasound system 100 and/or imager 112 may be utilized to detect signals from an acoustic reflector (e.g., microbubbles) located substantially close to the target region 101 as further described below. Additionally or alternatively, the system 100 may include an acoustic-signal detection device (such as a hydrophone or suitable alternative) 124 that detects transmitted or reflected ultrasound from the acoustic reflector, and which may provide the signals it receives to the controller 108 for further processing as further described below. In addition, the ultrasound system 100 may include an administration system 126 for parenterally introducing the acoustic reflector 202 into the patient's body. The imager 112, the acoustic-signal detection device 124, and/or the administration system 126 may be operated using the same controller 108 that facilitates the transducer operation; alternatively, they may be separately controlled by one or more separate controllers intercommunicating with one another.

Figure 1B:
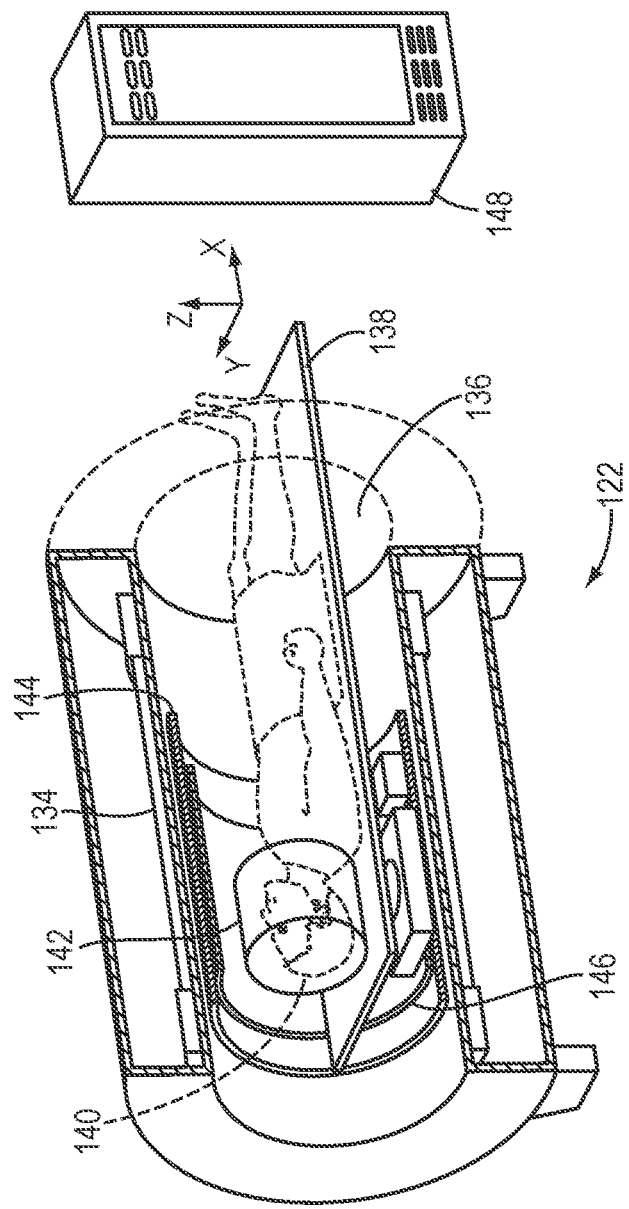
FIG. 1B schematically depicts an exemplary MRI system in accordance with various embodiments of the current invention.

FIG. 1B illustrates an exemplary imager—namely, an MRI apparatus 112. The apparatus 112 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 112 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region (e.g., a tumor or a target BBB) can be identified.

To perform targeted drug delivery or tumor ablation, it is necessary to determine the location of the target region 101 with high precision. Accordingly, in various embodiments, the imager 112 is first activated to acquire images of the target region 101 and/or non-target region (e.g., the healthy tissue surrounding the target region, the intervening tissue located between the transducer array 102 and the target region 101 and/or any regions located near the target) and, based thereon, determine anatomical characteristics (e.g., the tissue type, location, size, thickness, density, structure, shape, vascularization) associated therewith. For example, a tissue volume may be represented as a 3D set of voxels based on a 3D image or a series of 2D image slices and may include the target region 101 and/or non-target region.

Figure 2:
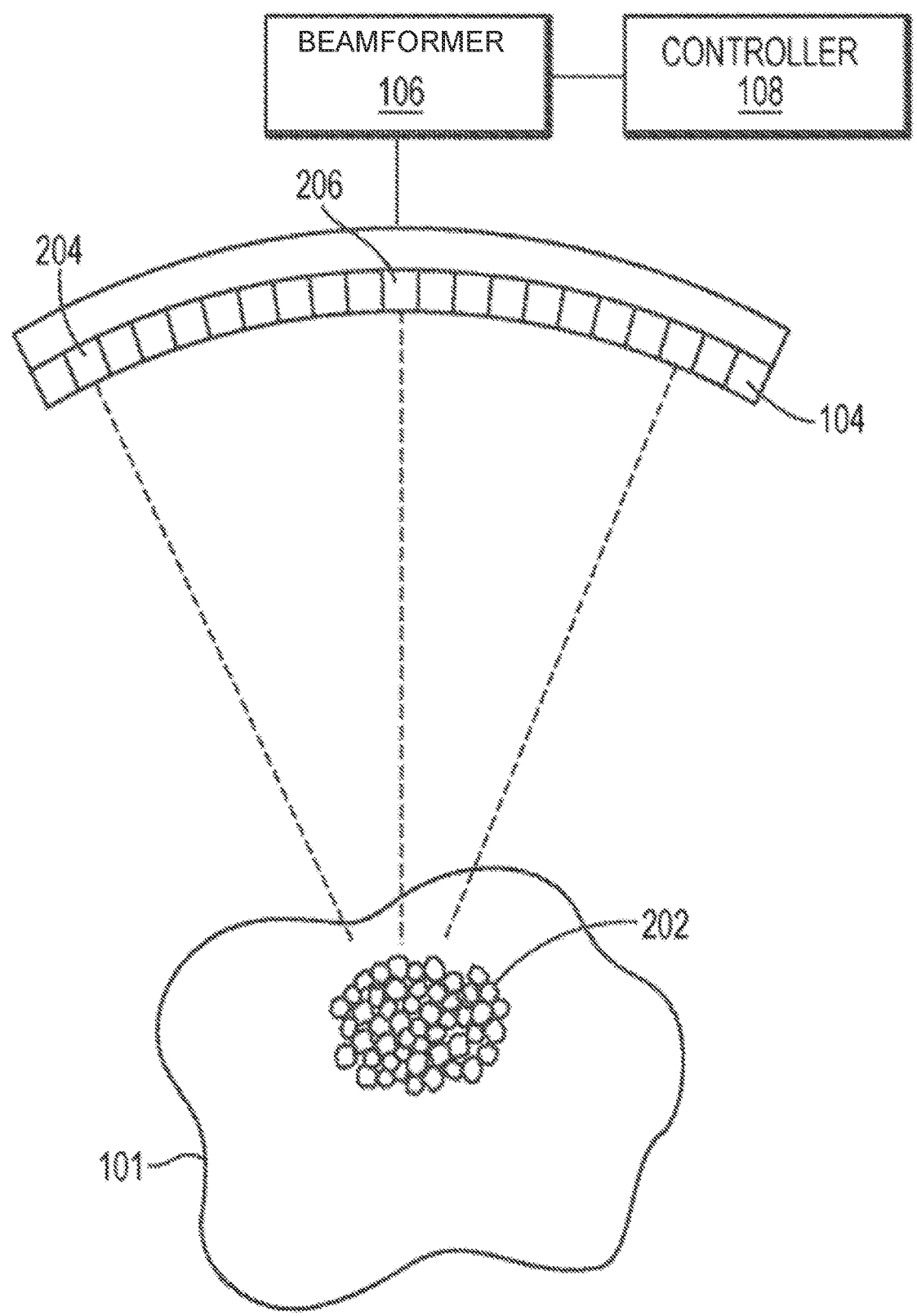
FIG. 2 depicts an implementation of an acoustic reflector substantially close to a target region for calibrating the transducer geometry and correcting beam aberrations in accordance with various embodiments.

To create a high-quality focus at the target region 101, it may be necessary to calibrate the transducer elements 104 and take into account transducer geometric imperfections resulting from, for example, movement, shifts and/or deformation of the transducer elements 104 from their expected locations. In addition, because the ultrasound waves may be scattered, absorbed, reflected and/or refracted when traveling through inhomogeneous intervening tissues located between the transducer elements 104 and the target region 101, accounting for these wave distortions may also be necessary in order to improve the focusing properties at the target region 101. Referring to FIG. 2, in various embodiments, calibration of the transducer geometry as well as correction of the beam aberrations caused by the inhomogeneous tissues are facilitated by employing an acoustic reflector 202 substantially close to the target region 101. Ultrasound waves transmitted from all (or at least some) transducer elements 104 are reflected by the reflector 202. The acoustic reflector 202 may consist essentially of microbubbles generated by the ultrasound waves and/or introduced parenterally by an administration system. In some embodiments, the administration device 126 introduces a seed microbubble into the target region 101; the transducer 102 is then activated to transmit ultrasound waves to the seed microbubble for generating a cloud of microbubbles. Approaches to generating the microbubbles and/or introducing the microbubbles to the target region 101 are provided, for example, in PCT Publication No. WO 2018/020315, PCT Application Nos. PCT/US2018/064058 (filed on Dec. 5, 2018), PCT/IB2018/001103 (filed on Aug. 14, 2018), PCT/US2018/064892 (filed on Dec. 11, 2018), PCT/IB2018/000841 (filed on Jun. 29, 2018), and PCT/US2018/064066 (filed on Dec. 5, 2018), U.S. Patent Publication No. 2019/0083065, and U.S. patent application Ser. No. 15/837,392 (filed on Dec. 11, 2017), the contents of which are incorporated herein by reference.

In some embodiments, the transducer elements 104 possess both transmit and detect capabilities; thus, the reflected signals from the acoustic reflector 202 can be detected by the transducer elements 104. Approaches to configuring the transducer elements for detecting the reflected signals are provided, for example, in the International Application entitled "Focused Ultrasound System with Optimized Monitoring of Cavitation" filed on even date herewith, the contents of which are incorporated herein by reference. Additionally or alternatively, the reflected signals from the acoustic reflector 202 may be detected using the acoustic-signal detection device 124 associated with the transducer elements. The measured signals may then be provided to the controller 108 to obtain information, such as the amplitudes and/or phases, associated with the reflections; these may be compared to the amplitudes and/or phases associated with the transmitted ultrasound waves from the transducer elements 104. Based on the deviations therebetween, the drive signals of the transducer elements 104 may be adjusted so as to compensate for the deviations, thereby improving the focusing properties. In some embodiments, this autofocusing procedure is iteratively performed until optimal focusing properties are achieved. Approaches for autofocusing an ultrasound beam at the target region are provided, for example, in PCT Publication No. WO 2018/020315 and U.S. Patent Application Nos. 62/781,258 (filed on Dec. 18, 2018); the entire contents of these applications are incorporated herein by reference.

Before being received by the transducer elements 104 and/or acoustic-signal detection device 124, however, the reflection signals from the acoustic reflector 202 have to traverse and interact with multiple layers of intervening tissue (e.g., the patient's brain tissue, skull and scalp). As a result, the signals detected by some transducer elements 204 and/or acoustic-signal detection device 124 may have poor quality, such as low SNRs and/or low repetitiveness (e.g., the differences among the determined ultrasound parameter values in repetitive measurements exceed 10% of one of the determined ultrasound parameter values) and the autofocusing approach described above may not be applicable to correct phases associated with these transducer elements 204. In various embodiments, upon determining that the SNRs of the signals received by the transducer elements and/or acoustic-signal detection device 124 are below a first predetermined threshold and/or the differences among the determined ultrasound parameter values in repetitive measurements equal or exceed a second predetermined threshold, such as 10%, of one of the determined ultrasound parameter values, the controller 108 may implement a physical model to predict parameter values (e.g., phases, amplitudes, and/or frequencies) associated with the transducer elements and drive them based on predicted values.

In one embodiment, the physical model employs an acoustic ray model to simulate the beam paths of ultrasound waves from the transducer elements 204 to the target region 101 based on, for example, the geometry of the transducer elements 204 and their locations and orientations relative to the target region 101. In addition, the acoustic ray model may take into account beam aberrations (e.g., refraction) resulting from the intervening tissues and adjust the beam paths to account for the aberrations. For example, the beam aberrations from the intervening tissues may be determined based on a speed of sound at the transmission frequency traversing the intervening tissues along the beam paths. The speed of sound may be estimated based on an empirical pre-clinical study, a sensor measurement performed in a pre-treatment procedure and/or reports obtained from known literature.

In various embodiments, the physical model further includes a focusing algorithm that determines the parameter values associated with the transducer elements based on the predicted beam paths between the elements and target region 101 such that constructive interference (i.e., a focus) of the ultrasound waves from the transducer elements occurs at the target region 101. In addition, the focusing algorithm may take into account the characteristics (e.g., structure, type, homogeneity, density, size, location, property, thickness, etc.) of the intervening tissue (determined using, for example, the imager 112 as described above) as these factors bear on aberrations of beams travelling therethough. Once the optimal ultrasound parameter values associated with the transducer elements for creating a focus with desired properties at the target region 101 are determined, the transducer elements 204 that receive reflection signals having low SNRs and/or low repetitiveness may be driven based on the parameter values computed using the physical model, whereas the transducer elements 206 that receive reflection signals having sufficient SNRs (e.g., equal to or above the first predetermined value) and/or high repetitiveness (e.g., the differences among the determined ultrasound parameter values in repetitive measurements are below the second predetermined value) may be driven based on the ultrasound parameter values corrected using the measured reflection signals from the acoustic reflector 202. Accordingly, by combining the reflection-signal measurements and model prediction, the present invention allows transmitted waves from both transducer elements 204, 206 that detect poor-quality signals and sufficient-quality signals, respectively, to be compensated for transducer geometric errors and/or beam aberrations resulting from the intervening tissues, thereby further improving the focusing properties at the target region 101.

In some embodiments, different imagers are employed to acquire information about different tissues (e.g., the intervening tissues and target tissue). For example, information of a targeted brain tumor may be obtained using MRI, whereas information of the intervening skull tissue may be acquired using CT imaging. In addition, spatial parameters (e.g., the orientations and positions) of the transducer elements 104 may be obtained using, for example, a time-of-flight approach in the ultrasound system. As a consequence, it may be necessary to register coordinate systems in different imaging modalities prior to employing the physical model to compute the ultrasound parameter values associated with the transducer elements. Exemplary registration approaches are provided, for example, in U.S. Pat. No. 9,934,570, the entire disclosures of which are hereby incorporated by reference.

Additionally or alternatively, the received reflection signals that have sufficient quality (e.g., SNRs and/or repetitiveness) may be utilized to optimize or improve the physical model for predicting the ultrasound parameter values associated with the transducer elements 204 that receive low-quality reflection signals. Generally, the physical model includes one or more model parameters (e.g., the speed of ultrasound waves traversing the intervening tissues or the phase bias caused by, for example, a temperature change). In one embodiment, the values of the model parameters are estimated based on the reflection signals having sufficient quality measured by the transducer elements 206. For example, the estimation approach may involve determining the model parameter values that allow the physical model to predict the phases associated with the transducer elements 206 matching (or at least having minimal deviations from) the actual measured values. Alternatively, the measured phases of the transducer elements 206 may be provided to the physical model, which inversely computes the required values for the model parameters. Again, the improved/optimized physical model may then be utilized to predict the ultrasound parameter values associated with the transducer elements 204 (i.e., transducer elements receiving low-quality reflection signals) for improving the focusing properties.

In some embodiments, the phases of the measured signals having sufficient quality (e.g., detected by the transducer elements 206 and/or acoustic-signal detection device 124) and various characteristics (e.g., the type, size, location, property, structure, thickness, density, etc.) of the intervening tissues along the beam paths may form a training set. Using the training set, a relationship between the observed tissue characteristics and measured phases can be determined by, for example, training a neural network (or other machine learning process such as a tree classifier or a Bayes classifier) either from scratch or by fine tuning using transfer learning. After training, the phases of the signals having low quality (e.g., detected by the transducer elements 204 and/or acoustic-signal detection device 124) may be predicted based on observed tissue characteristics using the trained neural network. Subsequently, the transducer elements 204 may be driven based on the predicted phases to improve the focusing properties at the target region 101. Exemplary approaches to creating the training set and predicting the ultrasound aberrations using the trained neural network are provided, for example, in PCT Publication No. WO 2018/011631, the entire disclosure of which is hereby incorporated by reference. In some embodiments, a method involving Keras tensorflow is implemented to train the neural network; this method may be particularly suitable for a small training dataset and/or fine-tuning a neural network trained using other approaches (see, e.g., http://cv-tricks.com/keras/fine-tuning-tensorflow/). Neural networks and training methodologies are well-characterized in the art and may be programmed and trained as described above without undue experimentation.

Figure 3:
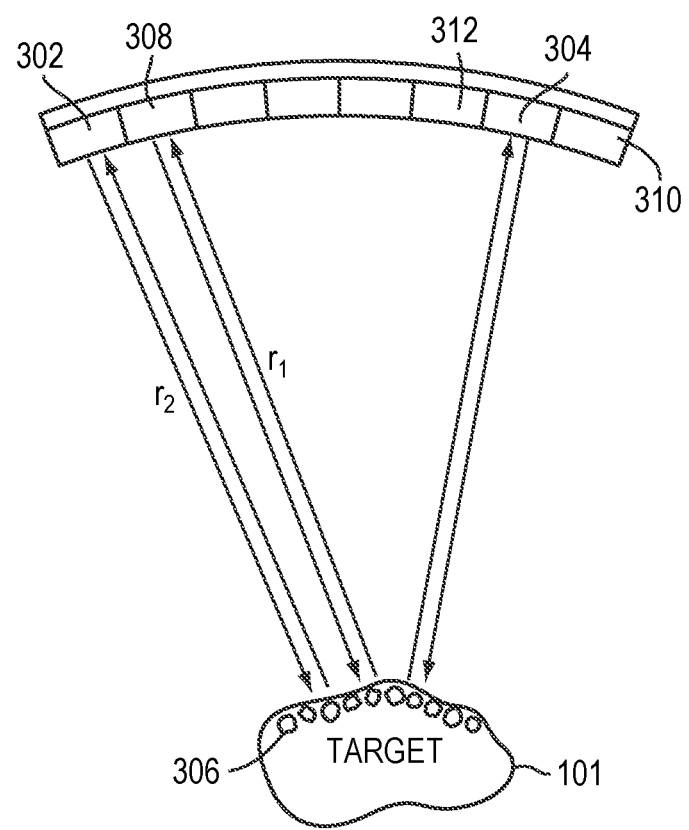
FIG. 3 depicts an approach for determining one or more ultrasound parameter values associated with a transducer element receiving low-quality reflection signals based on the reflection signals having sufficient quality in accordance with various embodiments.

In various embodiments, the ultrasound parameter values associated with the transducer elements 204 that receive low-quality reflection signals are determined based on the reflection signals that have sufficient quality. For example, with reference to FIG. 3, transducer elements 302, 304 may receive low-SNR reflection signals from an acoustic reflector 306 near the target 101; in one embodiment, the ultrasound parameter values of the elements 302, 304 are determined based on reflection signals having sufficient SNRs and received by one or more elements 308-312 located near the elements 302, 304. Assuming that the phase of the reflection signals measured by the transducer element 308 is $\varphi_{act1}$, the phase of the reflection signals associated with the element 302, $\varphi'_2$, may be computed as:

$$\varphi'_2 = \varphi_{act1} + \varphi_{g2} - \varphi_{g1},$$

where $\varphi_{g2}$ and $\varphi_{g1}$ represent computed phases associated with the reflection signals received by transducer elements 302, 308, respectively.

The phases $\varphi_{g2}$ and $\varphi_{g1}$ can be computed using any suitable approach. For example, because the measured phase $\varphi_{act1}$ includes aberrations of the ultrasound waves resulting from the intervening tissues, the phase difference between $\varphi_{g2}$ and $\varphi_{g1}$ (i.e., $\varphi_{g2} - \varphi_{g1}$) can be computed without considering effects on the phases resulting from the intervening tissues. To compute $\varphi_{g2} - \varphi_{g1}$, the ultrasound and MRI coordinate systems may first be registered as described above, the controller 108 may then determine the distances $r_1$ and $r_2$ from the target region 101 to the transducer elements 308, 302, respectively. Then based on the assumption that all transducer elements emit waves which can be approximated as spherical waves centered on the surface thereof, $\varphi_{g2} - \varphi_{g1}$ can be computed as:

$$\varphi_{g2} - \varphi_{g1} = \frac{2\pi f}{v}(r_2 - r_1),$$

where f represents a frequency of the reflection signals and v represents the speed of ultrasound waves in water or, in some embodiments, the average speed of ultrasound waves in tissue, which may be obtained either by a sensor using a time-of-flight approach or by lookup from the known literature. Accordingly, the phase of the reflection signals associated with the transducer element 302 may be computed as:

$$\varphi'_2 = \varphi_{act1} + \frac{2\pi f}{v}(r_2 - r_1). \qquad \text{Eq. (1)}$$

The controller 108 may then drive the transducer element 302 based on the determined phase $\varphi'_2$ so as to improve the focusing properties at the target region 101.

Generally, the phases of reflection signals received by the transducer elements 302, 304 may be determined based on the reflection signals received by one or more transducer elements that are located within a predetermined range. If more than one transducer element is used, an average of their computation results using Eq. (1) may be determined. For example, the transducer element 304 may have two elements 310, 312 that receive sufficient-SNR reflection signals and are located within the predetermined range; the phases of the reflection signals measured by the elements 310, 312 may be provided in Eq. (1) to compute the estimate phase associated with the element 304. In one embodiment, the average of the computed results can then be determined as the phase of waves associated with the element 304. In another embodiment, the phases of the transducer elements receiving low-SNR reflection signals are corrected based on a weighted average of the phases of the transducer elements receiving sufficient-SNR reflection signals. The weighting factor may be assigned based on, for example, the signal amplitudes measured in the transducer elements with sufficient SNRs and/or the geometric distance between the transducer element detecting a low SNR and the transducer elements detecting sufficient SNRs. This can be achieved by, for example, defining a weighting vector $\overline{w}$ having values of zero corresponding to the transducer elements that receive low-quality reflection signals and values greater than zero and less than or equal to one (i.e., $0<\overline{w}\leq 1$) corresponding to the transducer element(s) that receive sufficient-quality reflection signals. Additionally or alternatively, the weighting values corresponding to the transducer elements 308-312 may negatively correlate to the distances of the transducer elements 308-312 to the transducer elements 302, 304 receiving low-quality reflection signals. To correct the parameters associated with a transducer element, e, having low-quality reflection signals, the values of the weighting vector are applied to the respective parameter values (e.g., $\varphi'_2$ in Eq. (1)) associated with all other transducer elements (e.g., as a dot product); the result is then divided by the sum of the applied weighting values to obtain the final parameter value for transducer element e. In another embodiment, when information from more than two elements is used, a median filter can be used to select an optimal prediction for the phase of the element with the low SNR.

In some embodiments, a more sophisticated approach is applied to compute the phases $\varphi_{g2}$ and $\varphi_{g1}$. For example, the physical model described above may utilize the anatomical information (e.g., the type, size, location, property, structure, thickness, density, etc.) of the target and/or non-target regions. In one embodiment, a ray tracing model is used to better calculate the phase delay of the acoustic beam. In another embodiment, Snell's law is used to predict the additional phase delay due to beam refraction. In another embodiment, a full volume acoustic simulation is used to calculate the physical model (see, e.g., "Ultrasound Beam Simulations in Inhomogeneous Tissue Geometries Using the Hybrid Angular Spectrum Method," by Urvi Vyas and Douglas Christensen, published in *IEEE Transactions on Ultrasonics, Ferroelectrics, and Frequency Control*, volume 59, issue 6, June 2012).

In various embodiments, the transducer elements 302, 304 that receive low-quality reflection signals are identified in a remediation list stored, e.g., as a database in memory. To correct the ultrasound parameter values associated with each of the transducer elements on the remediation list, the controller 108 may search for one or more neighboring transducer elements that are located close by (e.g., within a predetermined distance) and that are not on the remediation list. Based on the reflection signals received by the neighboring transducer element(s) and the geometric distance(s) between the neighboring transducer element(s) and the transducer element on the remediation list, the ultrasound parameter value(s) associated with the transducer element on the remediation list can be adjusted (based on, e.g., Eq. (1)). In one embodiment, for each transducer element on the remediation list, one or more neighboring elements are identified (beginning with the closest) and, if the element(s) are not identified on the remediation list (or are instead, if preferred, identified on a separate list of transducer elements), their parameters are first adjusted based directly on the received reflection signals. The adjusted parameter values associated with the neighboring element(s) may then be transferred to that associated with the subject transducer element on the remediation list (using, e.g., Eq. (1)); that is, it may be sufficient to identify a single neighboring transducer element associated with adequate signal quality as a source of correction parameters, or it may be preferred to obtain and adjust parameters from multiple such neighboring transducer elements. For even greater convenience and faster operation, it may be preferred to maintain a database of transducer elements with fields, for each element, specifying whether the transducer element receives low-quality reflection signals and identifiers for its nearest neighboring transducer element(s). In this way, for any particular transducer on the remediation list, one or more source of correction (i.e., transducer elements that receive sufficient-quality reflection signals) can readily be identified.

The memory may include or consist essentially of one or more volatile or non-volatile storage devices, e.g., random-access memory (RAM) devices such as DRAM, SRAM, etc., read-only memory (ROM) devices, magnetic disks, optical disks, flash memory devices, and/or other solid-state memory devices. All or a portion of the memory may be located remotely from the ultrasound system 100 and/or the imager 112, e.g., as one or more storage devices connected to ultrasound system 100 and/or the imager 112 via a network (e.g., Ethernet, WiFi, a cellular telephone network, the Internet, or any local- or wide-area network or combination of networks capable of supporting data transfer and communication). As utilized herein, the term "storage" broadly connotes any form of digital storage, e.g., optical storage, magnetic storage, semiconductor storage, etc.

Figure 4A:
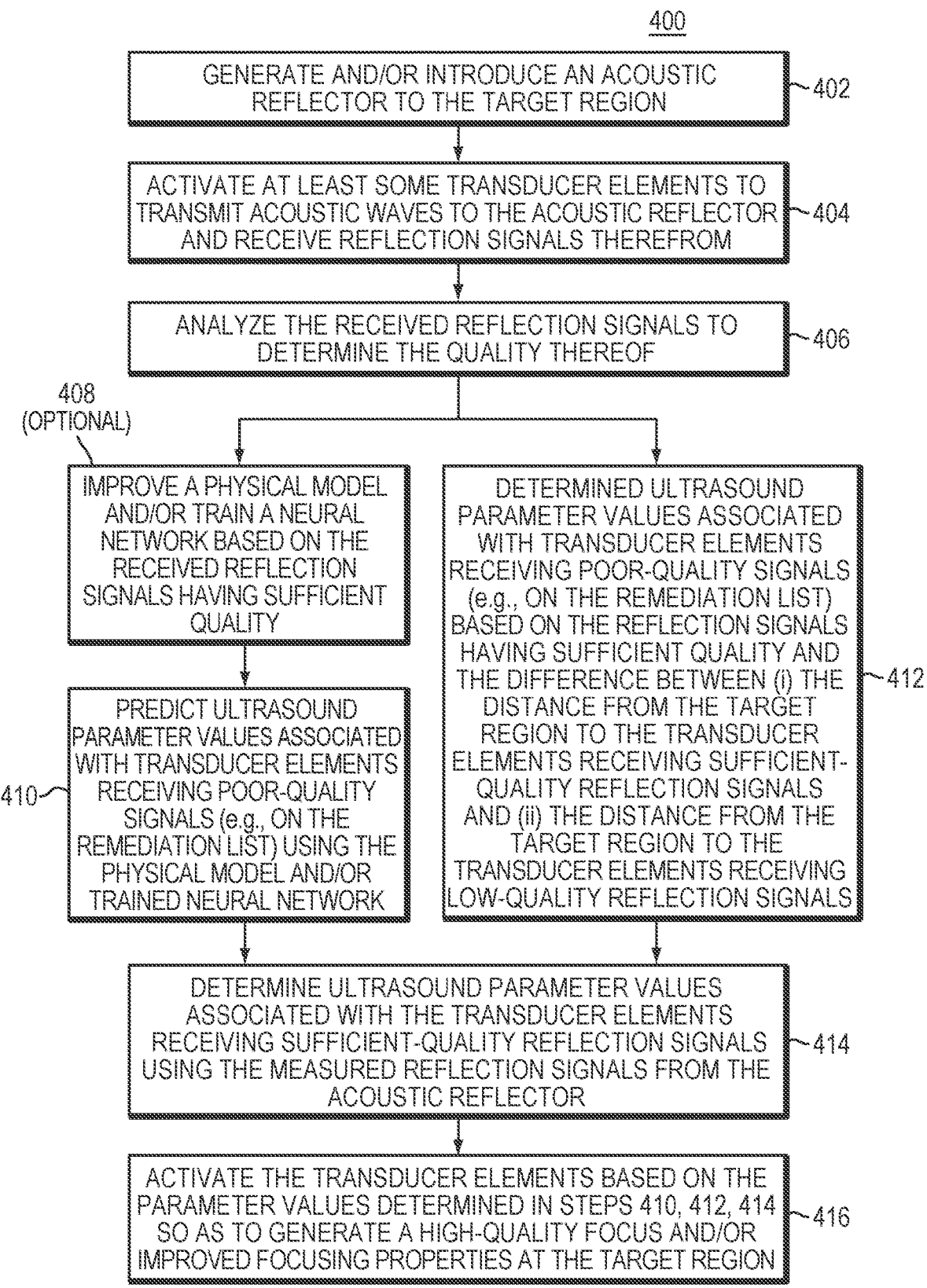
FIGS. 4A and 4B are flow charts illustrating exemplary approaches for compensating transducer geometric errors and/or beam aberrations resulting from intervening tissues, thereby improving focusing properties at a target region in accordance with various embodiments.

FIG. 4A is a flow chart illustrating an exemplary approach 400 for improving focusing properties at a target region in accordance herewith. In a first step 402, an acoustic reflector is generated and/or introduced into the target region. In a second step 404, at least some transducer elements are activated to transmit acoustic waves to the acoustic reflector and receive reflection signals therefrom. In one embodiment, one or more acoustic-signal detection devices 124 associated with the transducer elements are configured to receive the reflection signals. In a third step 406, the received reflection signals are analyzed to determine the quality thereof. Optionally, the received reflection signals that have sufficient quality may be used to improve a physical model and/or train a neural network (step 408). In one embodiment, the physical model and/or the trained neural network is then implemented to predict the ultrasound parameter values associated with the transducer elements that receive poor-quality signals (e.g., on the remediation list) (step 410). Alternatively, the ultrasound parameter values associated with the transducer elements that receive low-quality signals on the remediation list may be determined based on the reflection signals that have sufficient quality and the difference between (i) the distance from the target region to the transducer elements that receive sufficient-quality reflection signals and (ii) the distance from the target region to the transducer elements that receive low-quality reflection signals (step 412). In addition, the ultrasound parameter values associated with the transducer elements receiving sufficient-quality reflections signals may be determined using the measured reflection signals from the acoustic reflector (step 414). Subsequently, the transducer elements may be activated based on the parameter values determined above (steps 410, 412, 414) so as to generate a high-quality focus and/or improved focusing properties at the target region (step 416).

Figure 4B:
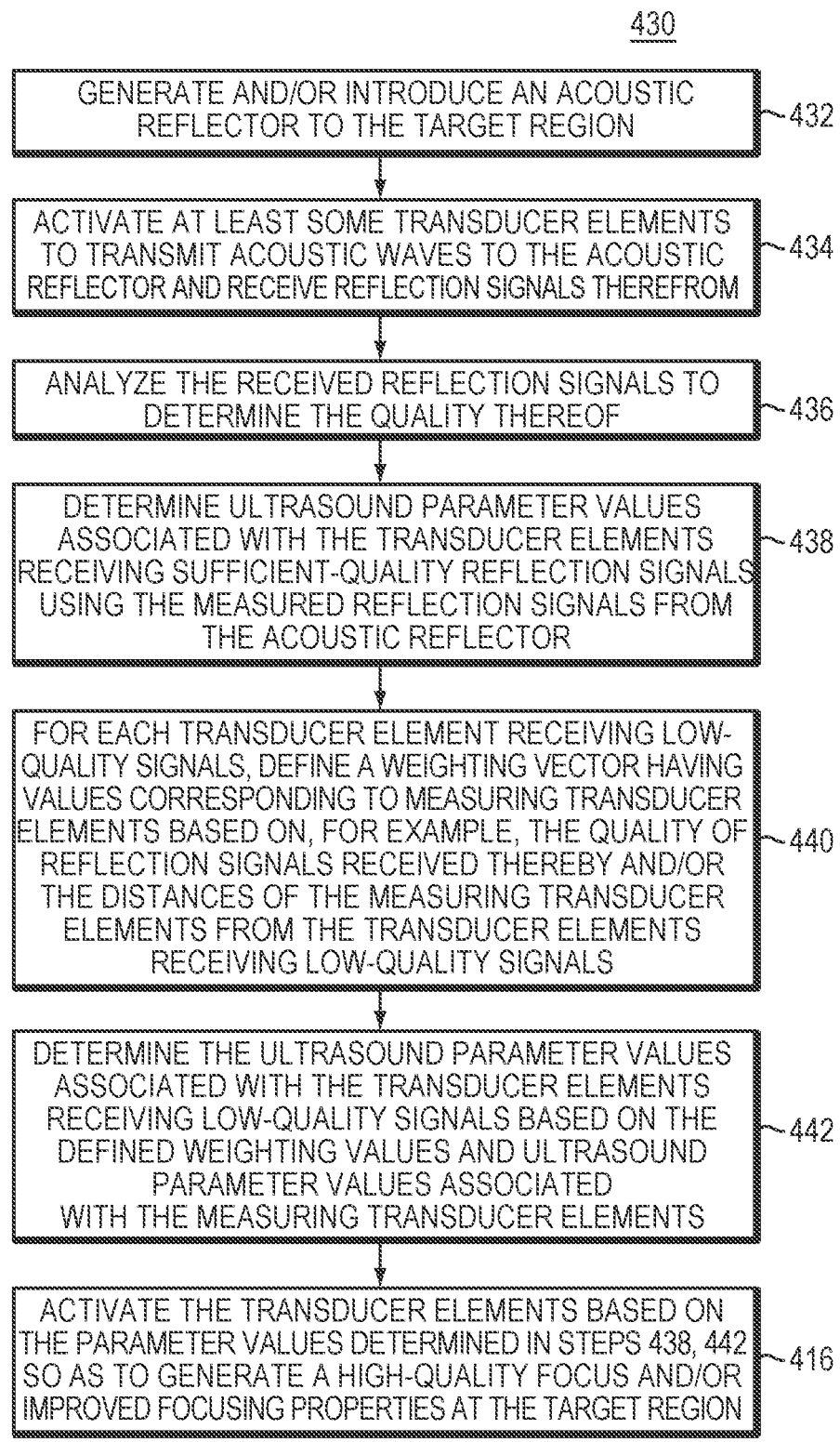

FIG. 4B is a flow chart illustrating another exemplary approach 430 for improving focusing properties at a target region in accordance herewith. In a first step 432, an acoustic reflector is generated and/or introduced into the target region. In a second step 434, at least some transducer elements are activated to transmit acoustic waves to the acoustic reflector and receive reflection signals therefrom. In one embodiment, one or more acoustic-signal detection devices 124 associated with the transducer elements are configured to receive the reflection signals. In a third step 436, the received reflection signals are analyzed to determine the quality thereof. If the reflection signals have sufficient quality, the ultrasound parameter values associated with the transducer elements receiving the sufficient-quality signals are determined based thereon (step 438). If the reflection signals have low quality, the ultrasound parameter values associated with the transducer elements receiving the low-quality signals may be determined based on the ultrasound parameter values associated with measuring transducer elements. For example, the controller 108 may assign weighting factors to the ultrasound parameter values associated with the measuring transducer elements based on, for example, the quality of reflection signals received thereby and/or the distances of the measuring elements from the transducer elements receiving low-quality signals (step 440). In some embodiments there is overlap between the transducer elements receiving low-quality signals and the measuring elements, and in other embodiments, the measuring transducer elements are different from the transducer elements receiving the low-quality signals. In one embodiment, the controller 108 defines a weighting vector having values of zero corresponding to the transducer elements that receive low-quality reflection signals, and values greater than zero and less than or equal to one corresponding to the transducer element(s) that receive sufficient-quality reflection signals. Additionally or alternatively, the weighting values corresponding to the transducer elements 308-312 may negatively correlate to the distances of the transducer elements 308-312 to the transducer elements 302, 304 receiving low-quality reflection signals. Subsequently, the values of the weighting vector are applied to the respective parameter values associated with all measuring transducer elements (e.g., as a dot product); the result is then divided by the sum of the applied weighting values to obtained the final parameter value for the transducer element detecting the low-quality reflection signals (step 442). The transducer elements are then activated based on the parameter values determined above (steps 438, 442) so as to generate a high-quality focus and/or improved focusing properties at the target region (step 416).

Figure 5A:
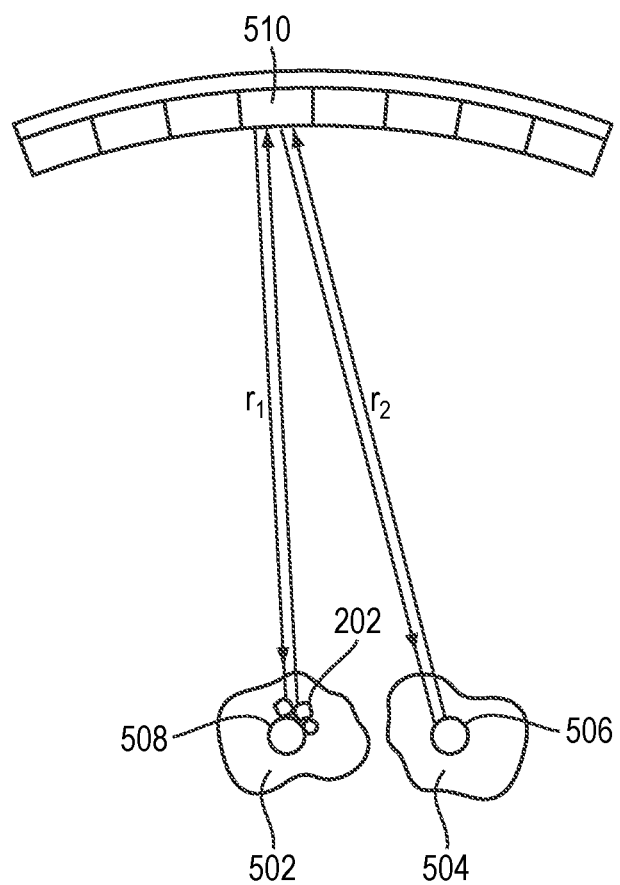
FIG. 5A depicts an approach for generating a high-quality focus at one target region based on the received reflection signals from another target region in accordance with various embodiments.

Referring to FIG. 5A, in some embodiments, the ultrasound treatment involves multiple discontiguous target regions 502, 504. While the autofocusing procedure described above may be applied at each of the target regions to improve the focusing properties, the entire process may be time consuming. Accordingly, the ultrasound parameter values for treating one target region (e.g., the region 504) may be determined based on those used for treating another target region(s) (e.g., the region 502) located close by (e.g., within a predetermined range of distance which, based on a known tissue response to applied ultrasound energy, will result in the nearby tissue reaching a therapeutic temperature). For example, the physical model described above may predict the ultrasound parameter values of the transducer elements for creating a focus 506 at the target region 504 based on the measured reflection signals from the acoustic reflector 202 located substantially close to the target region 502. In various embodiments, assuming that $\varphi_{act1}$ is the measured phase of the reflection signals from the acoustic reflector 202 at the target region 502 by the element 510, the phase of the reflection signals associated with the element 510 from the target region 504, $\varphi'_2$, may be computed as:

$$\varphi'_2 = \varphi_{act1} + \varphi_{g2} - \varphi_{g1},$$

where $\varphi_{g1}$ and $\varphi_{g2}$ represent computed phases associated with the reflection signals received by the transducer element 510 from the target regions 502, 504, respectively.

Again, the phases $\varphi_{g2}$ and $\varphi_{g1}$ can be computed using any suitable approach. Similar to the approach described with respect to FIGS. 3 and 4, the phase difference between $\varphi_{g2}$ and $\varphi_{g1}$ (i.e., $\varphi_{g2} - \varphi_{g1}$) here may be computed without considering the effects on the phases resulting from the intervening tissues (because these effects have been accounted for in the measured phase $\varphi_{act1}$). In addition, by assuming that the transducer element 510 emits spherical waves centered on the surface thereof, $\varphi_{g2} - \varphi_{g1}$ can be computed as:

$$\varphi_{g2} - \varphi_{g1} = \frac{2\pi f}{v}(r_2 - r_1),$$

where $r_1$ and $r_2$ represent the distances from the transducer element 510 to the target regions 502, 504, respectively, f represents a frequency of the reflection signals and v represents a speed of ultrasound waves in water. As a result, the phase of the reflection signals associated with the element 510 from the target region 504 may be computed as:

$$\varphi'_2 = \varphi_{act1} + \frac{2\pi f}{v}(r_2 - r_1). \quad \text{Eq. (2)}$$

Figure 5B:
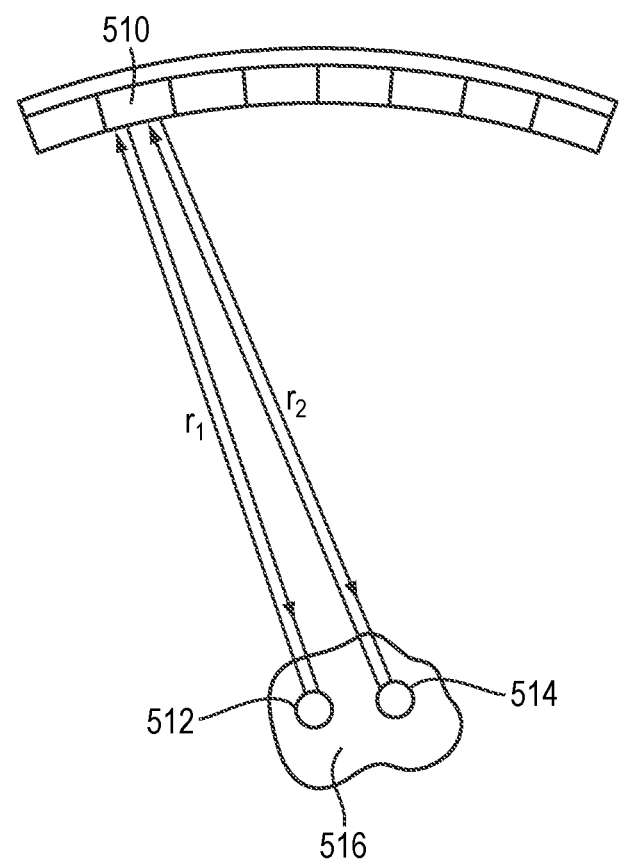
FIG. 5B depicts an approach for generating a high-quality focus at a target region based on the received reflection signals from another focus within the same target region in accordance with various embodiments.

This approach may be iteratively performed to estimate the phases associated with all transducer elements for collectively creating the focus 406 with optimal focusing properties at the target region 504. Subsequently, the transducer elements may be driven based on the computed phases. Although the approach described above involves multiple target regions 502, 504, it can be applied to create multiple high-quality discrete foci 512, 514 located within a single target region 516 (e.g., during beam steering) as well (FIG. 5B).

In some embodiments, the physical model optimized or improved using the reflection signals from the target region 502 is implemented to predict the ultrasound parameter values for generating the focus 506 at the target region 504. For example, similar to the approach described above, the physical model may first estimate or adjust the model parameter values based on the reflections from the target region 502. Based on the estimated/adjusted values, the physical model may predict the phases associated with the transducer elements for generating the focus 506 at the target region 504.

Further, the measured phases of the signals from the acoustic reflector 202 at the target region 502 and various characteristics (e.g., the type, size, location, property, structure, thickness, density, etc.) of the intervening tissues (acquired, e.g., using the imager 112) may form a training set. By training a neural network (or other machine learning process) using the training set, a relationship between the observed tissue characteristics and measured phases can be determined as described above. After training, the phases of the waves from the target region 504 may be predicted using the trained neural network. Again, the transducer elements may then be driven based on the predicted phases so as to create a high-quality focus at the target region 504.

Figure 6:
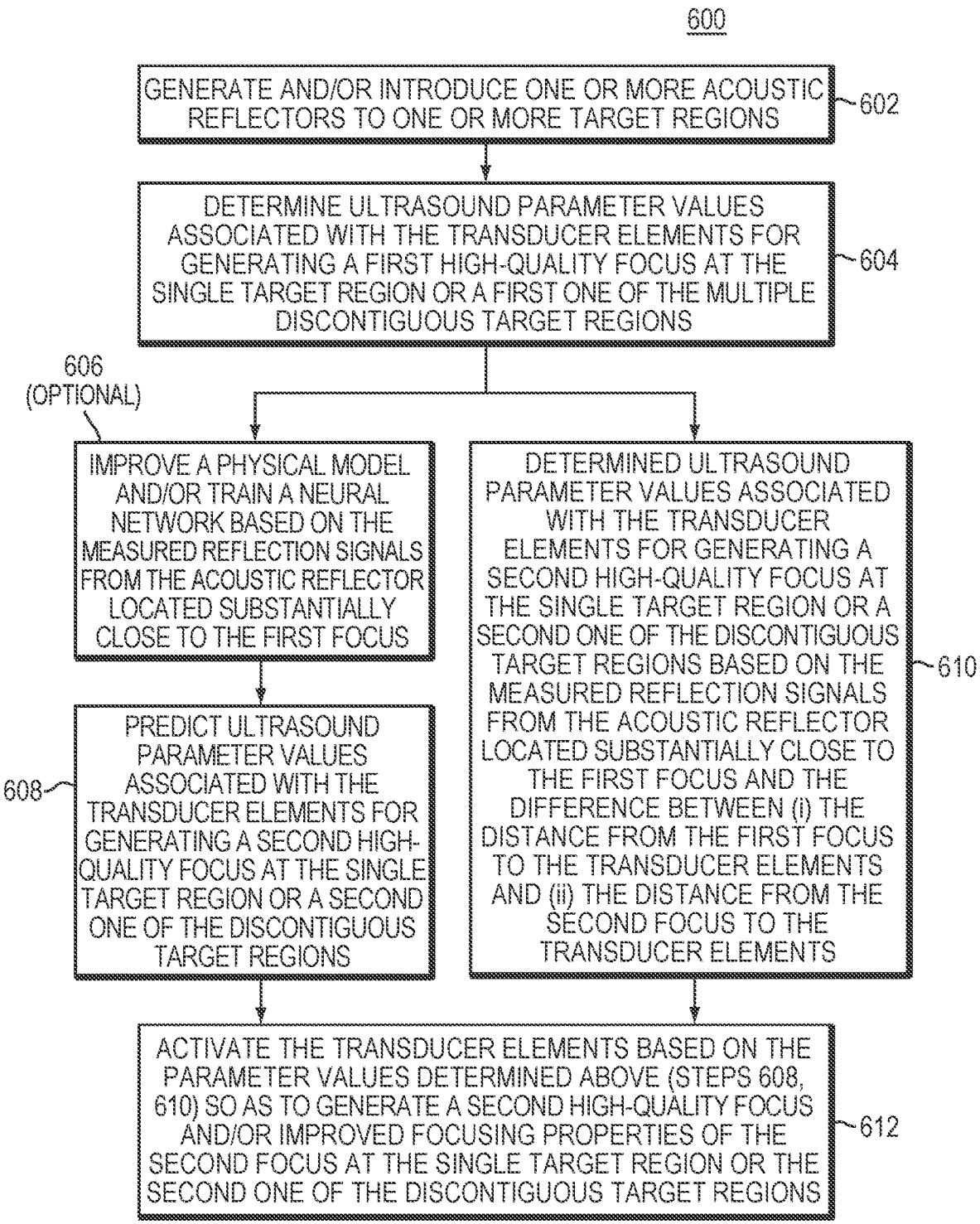
FIG. 6 is a flow chart illustrating an exemplary approach for compensating transducer geometric errors and/or beam aberrations resulting from intervening tissues, thereby improving focusing properties of one or more foci at one or more target regions in accordance with various embodiments.

FIG. 6 is a flow chart illustrating an exemplary approach 600 for improving focusing properties of one or more foci at one or more target regions in accordance herewith. In a first step 602, one or more acoustic reflectors are generated and/or introduced into one or more target regions (e.g., a single target region or multiple discontiguous target regions). In a second step 604, the ultrasound parameter values associated with the transducer elements for generating a first high-quality focus at the single target region or a first one of the multiple discontiguous target regions are determined. In some embodiments, the ultrasound parameter values are determined using the approaches described in FIGS. 4A and 4B. Optionally, the measured reflection signals from the acoustic reflector located substantially close to the first focus may be utilized to improve the physical model and/or train the neural network (step 606). In one embodiment, the physical model and/or the trained neural network is then implemented to predict the ultrasound parameter values associated with the transducer elements for generating a second high-quality focus at the single target region or a second one of the discontiguous target regions (step 608). Alternatively, the ultrasound parameter values associated with the transducer elements for generating the second high-quality focus at the single target region or the second one of the discontiguous target regions may be determined based on the measured reflection signals from the acoustic reflector located substantially close to the first focus and the difference between (i) the distance from the first focus to the transducer elements and (ii) the distance from the second focus to the transducer elements (step 610). Subsequently, the transducer elements may be activated based on the parameter values determined above (steps 608, 610) so as to generate a second high-quality focus and/or improved focusing properties of the second focus at the single target region or the second one of the discontiguous target regions (step 612).

In general, functionality for facilitating an acoustic-reflector-mediated ultrasound procedure for generating a high-quality focus and/or improved focusing properties at one or more target regions may be structured in one or more modules implemented in hardware, software, or a combination of both, whether integrated within a controller of the ultrasound system 100, an imager 112, and/or the administration system 126, or provided by a separate external controller or other computational entity or entities. Such functionality may include, for example, analyzing imaging data of the target and/or non-target regions acquired using an imager 112, determining a region of the target tissue and/or non-target tissue based on the imaging data, determining the anatomical characteristics (e.g., the tissue type, location, size, thickness, density, structure, shape, vascularization) associated with the target/non-target tissue, activating at least some transducer elements to transmit acoustic waves to the acoustic reflector and receive reflection signals therefrom, causing an acoustic-signal detection device 124 to receive the reflection signals, analyzing the received reflection signals to determine the quality thereof, improving a physical model and/or training a neural network based on the received reflection signals having sufficient quality, predicting the ultrasound parameter values associated with transducer elements that receive poor-quality signals using the physical model and/or trained neural network, determining the ultrasound parameter values associated with transducer elements that receive poor-quality signals based on the reflection signals having sufficient quality and the difference between (i) the distance from the target region to the transducer elements receiving sufficient-quality reflection signals and (ii) the distance from the target region to the transducer elements receiving low-quality reflection signals, determining ultrasound parameter values associated with the transducer elements that receive sufficient-quality reflections signals using the measured reflection signals from the acoustic reflector, for each transducer element receiving low-quality signals, defining a weighting vector having multiple values corresponding to measuring transducer elements based on, for example, the qualities of reflection signals received thereby and/or the distances of the measuring elements from the transducer elements receiving low-quality signals, determining the ultrasound parameter values associated with the transducer elements receiving low-quality signals based on the defined weighting values and ultrasound parameter values associated with the measuring transducer elements, activating the transducer elements based on the determined parameter values so as to generate a high-quality focus and/or improved focusing properties at the target region, determining ultrasound parameter values associated with the transducer elements for generating a first high-quality focus at a single target region or a first one of the multiple discontiguous target regions, improving a physical model and/or train a neural network based on the measured reflection signals from the acoustic reflector located substantially close to the first focus, predicting the ultrasound parameter values associated with the transducer elements for generating a second high-quality focus at the single target region or a second one of the discontiguous target regions using the physical model and/or trained neural network, determining the ultrasound parameter values associated with the transducer elements for generating a second high-quality focus at the single target region or a second one of the discontiguous target regions based on the measured reflection signals from the acoustic reflector located substantially close to the first focus and the difference between (i) the distance from the first focus to the transducer elements and (ii) the distance from the second focus to the transducer elements, and activating the transducer elements based on the determined parameter values so as to generate a second high-quality focus and/or improved focusing properties of the second focus at the single target region or the second one of the discontiguous target regions, as described above.

In addition, the ultrasound controller 108, the MR controller 148 and/or the controller associated with the administration system 126 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for focusing an ultrasound transducer comprising:
    an ultrasound transducer comprising a plurality of transducer elements; and
    a controller configured to:
        cause the plurality of transducer elements to transmit ultrasound waves to a target regions;
        cause measuring transducer elements included in the plurality of transducer elements of the ultrasound transducer to measure reflections of the ultrasound waves transmitted by the plurality of transducer elements of the ultrasound transducer off the target region;
        weight parameter values corresponding to the measuring transducer elements at least in part by signal quality metrics associated with the reflections measured by the measuring transducer elements;
        for each transducer element of at least some of the plurality of transducer elements, adjust a parameter value corresponding to said each transducer element based at least in part on the weighted parameter values corresponding to a plurality of the measuring transducer elements; and
        cause said each transducer element to transmit ultrasound waves to the target region using the adjusted parameter values corresponding to said each transducer element so as to increase acoustic intensity at the target region.

2. The system of claim 1, wherein the controller is further configured to define a weighting vector having values of zero corresponding to measuring transducer elements that measure reflections having signal quality metrics below a predetermined threshold.

3. The system of claim 1, wherein the controller is further configured to define a weighting vector having values greater than zero and less than or equal to one corresponding to measuring transducer elements that measure reflections having signal quality metrics equal to or exceeding a predetermined threshold.

4. The system of claim 1, wherein the controller is further configured to:
weight the parameter values corresponding to the measuring transducer elements at least in part by distances between the measuring transducer elements and a transducer element of said each transducer element whose parameter value is adjusted.

5. The system of claim 4, wherein the weighting values corresponding to the measuring transducer elements negatively correlate to the distances.

6. The system of claim 1, wherein the measuring transducer elements are different from said each transducer element, and the measuring transducer elements and said each transducer element are all included in the plurality of transducer elements of the ultrasound transducer.

7. The system of claim 1, wherein the signal quality metric is a signal-to-noise ratio of the measured reflections.

8. The system of claim 1, wherein the signal quality metric is repetitiveness of the parameter value corresponding to one of the measuring transducer elements determined based on the measured reflections in a plurality of measurements.

9. The system of claim 1, wherein the controller is further configured to cause generation of at least one acoustic reflector in the target region using the ultrasound transducer, the acoustic reflector reflecting the ultrasound waves transmitted thereto.

10. The system of claim 1, further comprising an administration device for introducing at least one acoustic reflector into the target region.

11. The system of claim 1, further comprising an administration device for introducing a seed microbubble into the target region, wherein the controller is further configured to cause generation of at least one acoustic reflector using the seed microbubble and the ultrasound transducer, the acoustic reflector reflecting the ultrasound waves transmitted thereto.

12. The system of claim 1, wherein the controller is further configured to adjust at least one of the parameter values corresponding to one of the measuring transducer elements based at least in part on the reflections measured thereby.

13. The system of claim 1, wherein the controller is further configured to adjust the parameter value corresponding to said each transducer element based at least in part on a physical model.

14. The system of claim 13, wherein the physical model comprises a plurality of model parameters, the controller being further configured to determine values corresponding to the model parameters based at least in part on the reflections measured by at least one of the measuring transducer elements.

15. The system of claim 1, wherein the controller is further configured to adjust the parameter value corresponding to said each transducer element based at least in part on a predictor that has been computationally trained to predict the parameter value based on a characteristic of an intervening tissue located between said each transducer element and the target region.

16. The system of claim 15, wherein the controller is further configured to computationally train the predictor using the reflections measured by at least one of the measuring transducer elements and the characteristic of the intervening tissue located between the at least one of the measuring transducer elements and the target region.

17. The system of claim 15, further comprising an imaging modality for acquiring the characteristic of the intervening tissue.

18. The system of claim 1, wherein the parameter value comprises a frequency, an amplitude or a phase.

19. The system of claim 1, wherein the controller is further configured to:
compute a first phase corresponding to at least one of the measuring transducer elements and a second phase corresponding to said each transducer element; and
adjust the parameter value corresponding to said each transducer element based at least in part on the computed first and second phases.

20. The system of claim 19, wherein the controller is further configured to compute a difference between the first and second phases based at least in part on a difference between a first distance from the at least one of the measuring transducer elements to the target and a second distance from said each transducer element to the target.

21. The system of claim 20, wherein the controller is further configured to compute the first phase based at least in part on a characteristic of an intervening tissue located between the at least one of the measuring transducer elements and the target region along a beam path corresponding to the reflections measured by the at least one of the measuring transducer elements.

* * * * *